Dec. 12, 1972 C. G. KLEHM Plant Pat. 3,270
PEONY PLANT
Filed Feb. 22, 1971
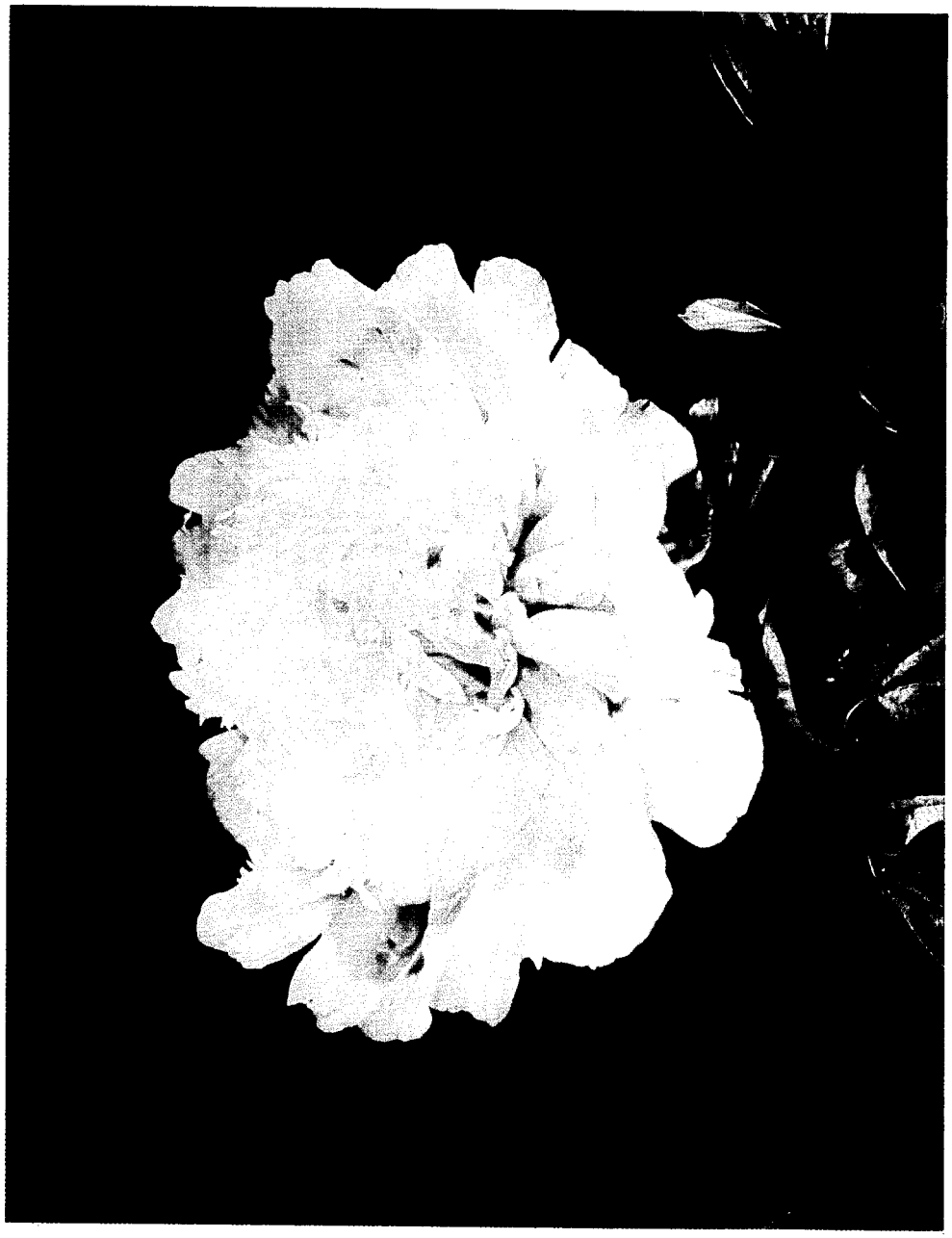
Inventor.
Carl G. Klehm
By: Robb & Robb
Attorneys.

United States Patent Office

Plant Pat. 3,270
Patented Dec. 12, 1972

3,270
PEONY PLANT

Carl G. Klehm, 2 E. Algonquin Road,
Arlington Heights, Ill. 60005
Filed Feb. 22, 1971, Ser. No. 117,845
Int. Cl. A01h 5/00
U.S. Cl. Plt.—68 1 Claim The present invention relates to a new and distinct variety of peony plant of the species botanically known as *Paeonia lactiflora,* which was originated by me by crossing an unnamed and unpatented "bull" type peony seedling, identified in my breeding records as No. 71D, with the peony variety known as "Mons. Jules Elie" (unpatented), the unnamed seedling being the male parent and "Mons. Jules Elie" being the female parent.

My new variety resulted from an extensive and prolonged program of breeding and testing conducted by me in an effort to produce new and improved or unique peony varieties, and was selected as one of many outstanding varieties resulting from this breeding program because of its unique combination of the following principal characteristics which distinguish the new variety from its parents, as well as from all other peony varieties of which I am aware:

(1) A short but strong habit of growth;

(2) A balanced, vigorous, clean and disease-free root system;

(3) Disease-free shoots, stems and foliage of a lush, bright green color;

(4) A medium flower size;

(5) A frilly and ruffled bomb-shaped flower form, with slightly atropic carpels and no stamens;

(6) A distinctive and attractive color of the flowers which have a double row of pure white, notched guard petals dorsalled with 6 to 9 rows of lemon yellow petaloids and true petals which are dorsalled again with 15 to 30 slightly larger and ruffled light pink petals; and (7) Especial suitability for cut-flower and garden landscape uses, and for borders and backdrops for other flower settings.

Asexual reproduction of my new peony variety by root division, as performed by me in my nursery located at Arlington Heights, Ill., shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 Edition), published by The Royal Horticultural Society, of London, England, as based on specimens grown and observed by me at Arlington Heights and Barrington, Illinois:

Breeding: Seedling.
- *Seed parent.*—"Mons. Jules Elie."
- *Pollen parent.*—An unnamed seedling identified as No. 71D and which was a line-bred progeny of the seed parent.

Propagation: Holds its distinguishing characteristics through succeeding propagations by root division.

Flower

Blooming habits: Annual.
Blooming season: Considered early to early mid-season.
Bud:
- *Size.*—Medium large.
- *Form.*—Smooth; round.

- *Color.*—Orient pink, Fan 1, Plate 36 D'.
- *Sepals.*—Smooth; even edge.
  - Color—Green.
- *Calyx.*—Polysepalous.
- *Opening.*—Opens smoothly and easily.

Bloom:
- *Size.*—Medium; from about 6 inches to 6½ inches in diameter.
- *Borne.*—Singly, with 3 auxiliary buds.
- *Stems.*—Strong; about 30 inches tall.
- *Form.*—Frilly bomb-shaped.
- *Petalage.*—Double.
- *Color.*—An unusual combination of white, lemon yellow and light pink, corresponding to Fan 4, Plate 155B, Fan 1, Plate 8A, and Fan 1, Plate 36D.
- *Variegations.*—None.
- *Discolorations.*—None.

Petals:
- *Texture.*—Medium.
- *Appearance.*—Shiny.
- *Form.*—Ruffled; notched; frilled.
- *Arrangement.*—Imbricated by frills.
- *Persistence.*—Above average.
- *Fragrance.*—Slight peony fragrance.
- *Lasting qualities.*—Above average.

*Reproductive organs*

Organs:
- *Male.*—None.
- *Female.*—Slightly atropic stigmas and styles.

Fruit: None.

Plant

Form: Bush.
Growth: Healthy; strong; lush.
Foliage:
- *Leaflets.*—From 5 to 7 in number.
- *Size.*—Medium.
- *Quantity.*—Above average.
- *Color.*—Green Beetle, Fan 3, Plate 135 B'.
- *Shape.*—Elliptically acute.
- *Texture.*—Dorsal is glossy, with pronounced veins.
- *Edge.*—Smooth.
- *Serrations.*—None.
- *Leaf stems.*—Thick; succulent.
- *Stipules.*—None.
- *Disease resistance.*—Resistant to leaf blotch and other bacterial peony diseases, as determined by comparison with other varieties for many years as grown at Arlington Heights and Barrington, Ill.

*General observations*

The new variety is distinctively unique primarily because of its succulent, robust and vigorous growth habit, clean foliage, and unusual white, pink and yellow flower color combination which is an extremely attractive and delicate color combination rarely found in any flower species.

I claim:

1. A new and distinct variety of peony plant of the species botanically known as *Paeonia lactiflora,* substantially as herein shown and described, characterized particularly as to novelty by the unique combination of a short but strong habit of growth, a balanced, vigorous, clean and disease-free root system, disease-free shoots, stems and foliage of a lush, bright green color, a medium flower size, a frilly and ruffled bomb-shaped flower form, with slightly atropic carpels and no stamens, a distinctive and attractive color of the flowers which have a double row of pure white, notched guard petals dorsalled with 6 to 9 rows of lemon yellow petaloids and true petals which are dorsalled again with 15 to 30 slightly larger and ruffled light pink petals, and especial suitability for cut-flower and garden landscape uses, and for borders and backdrops for other flower settings.

No references cited.

ROBERT E. BAGWILL, Primary Examiner